United States Patent [19]

Narula et al.

[11] Patent Number: 4,985,402
[45] Date of Patent: Jan. 15, 1991

[54] 2-METHYL-1-NITRILO-OR 2-METHYL-1-HYDROXYLAMINO-3-(METHOXYPHENYL) PROPANE, ORGANOLEPTIC USES THEREOF AND PROCESSES FOR PREPARING SAME

[75] Inventors: Anubhav P. S. Narula, Hazlet; De Virgilio John J., Freehold, both of N.J.

[73] Assignee: International Flavors & Fragrances Inc., New York, N.Y.

[21] Appl. No.: 514,514

[22] Filed: Apr. 25, 1990

[51] Int. Cl.$^5$ .............................................. A61K 7/46
[52] U.S. Cl. .......................................... 512/6; 512/20; 564/265; 558/410; 252/174.11; 252/187.24
[58] Field of Search ............... 512/6, 20, 12; 564/265; 558/410; 252/174.11, 187.24

[56] References Cited

U.S. PATENT DOCUMENTS

| | | | |
|---|---|---|---|
| 3,168,550 | 2/1965 | Blumenthal | 512/6 |
| 3,325,369 | 6/1967 | Somerville et al. | 512/6 |
| 4,040,986 | 8/1977 | Boelens et al. | 512/6 |
| 4,377,533 | 3/1983 | Bouisset et al. | 260/465.1 |
| 4,459,224 | 7/1984 | van der Weerdt et al. | 512/6 |
| 4,490,284 | 12/1984 | Brunke et al. | 512/6 |
| 4,560,690 | 12/1985 | Reiter | 514/256 |

OTHER PUBLICATIONS

Chem. Abstracts, vol. 84:79589q (Brud, et al.), 1976.
Arctander, "Perfume and Flavor Chemicals (Aroma Chemicals)", II, 1969, Monograph 2597.

Primary Examiner—James H. Reamer
Attorney, Agent, or Firm—Arthur L. Liberman

[57] ABSTRACT

Described are 2-methyl-1-nitrilo- or 2-methyl-1-hydroxylamino-3-(methoxyphenyl) propanes defined according to the generic structure:

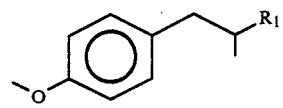

wherein $R_1$ is selected from the group consisting of: (i) cyanide having the structure:

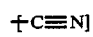

(ii) hydroxylaminomethyl having the structure:

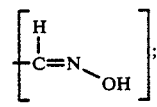

uses thereof in augmenting or enhancing the aroma of perfume compositions, colognes and perfumed articles including but not limited to bleach compositions, solid or liquid anionic, cationic, nonionic or zwitterionic detergents, perfumed polymers, fabric softener compositions, fabric softener articles, cosmetic powders and hair preparations. Also described are processes for preparing such 2-methyl-1-nitrillo- or 2-methyl-1-hydroxylamino-3-(methoxyphenyl) propanes by means of reacting a methoxy benzyl halide with ethyl cyanide in the presence of a basic catalyst such as sodamide.

10 Claims, 7 Drawing Sheets

GLC PROFILE FOR EXAMPLE I.

IR SPECTRUM FOR EXAMPLE I.

GLC PROFILE FOR EXAMPLE II.

FIG. 5 NMR SPECTRUM FOR EXAMPLE II.

IR SPECTRUM FOR EXAMPLE II.

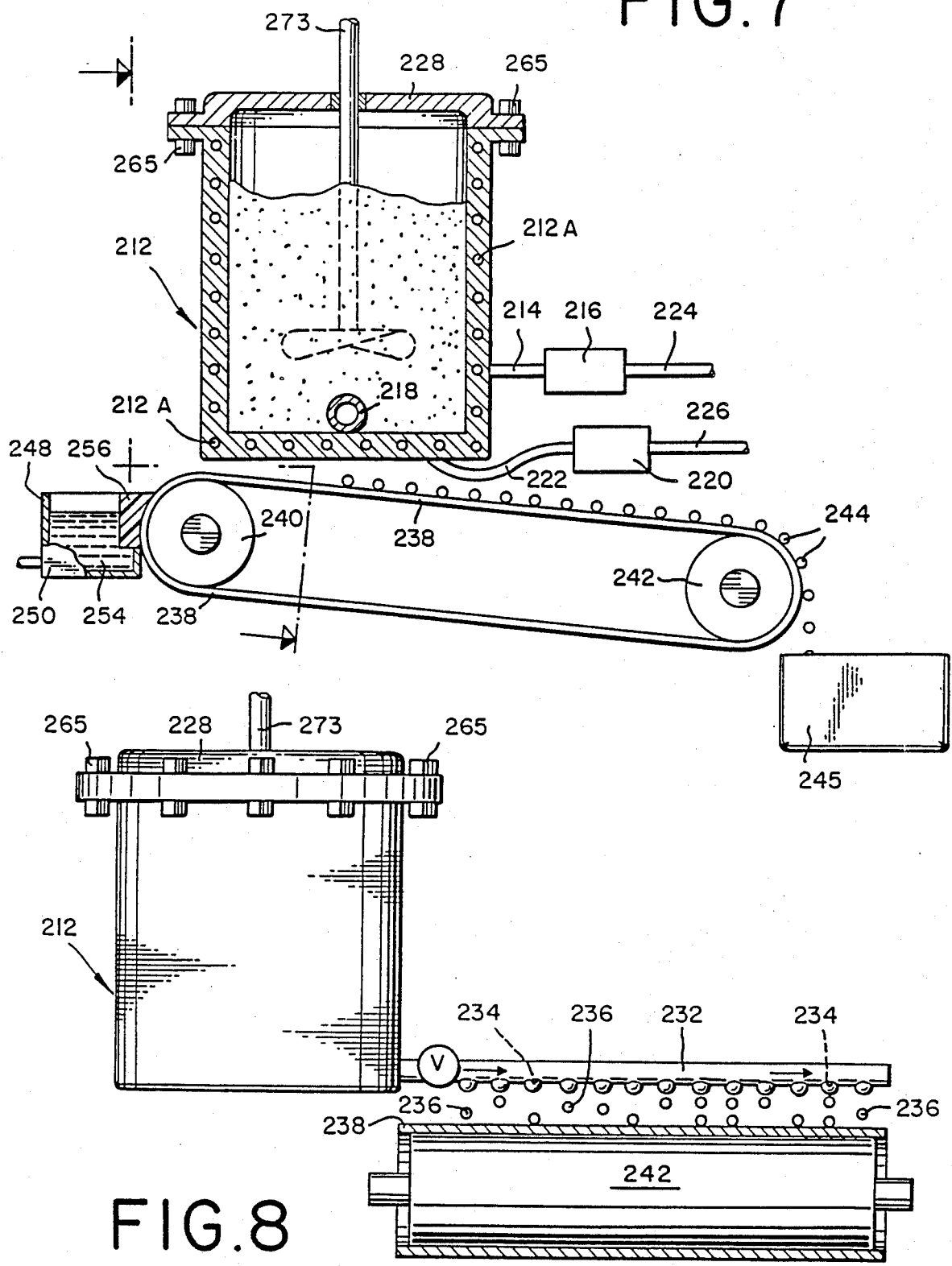

2-METHYL-1-NITRILO-OR 2-METHYL-1-HYDROXYLAMINO-3-(METHOXYPHENYL) PROPANE, ORGANOLEPTIC USES THEREOF AND PROCESSES FOR PREPARING SAME

BACKGROUND OF THE INVENTION

The present invention relates to 2-methyl-1-nitrilo- or 2-methyl-1-hydroxylamino-3-(methoxyphenyl) propanes defined according to the structure:

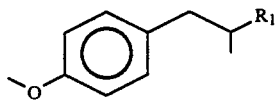

wherein $R_1$ is a nitrogen-containing moiety selected from the group consisting of:

(i) cyanide having the structure:

and (ii) hydroxylaminomethyl having the structure:

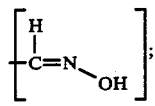

as well as uses thereof in order to alter, modify, or enhance the aroma of a consumable material.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting and substantive sweet, anisic, animalic aromas with sweet and anisic topnotes are highly desirable in several types of perfume compositions, perfumed articles and colognes (e.g., hawthorn blossom perfumes or lilac perfumes).

The perfume uses of nitrile-containing derivatives which also contain phenyl moieties is well known in the prior art. Thus, U.S. Pat. No. 3,325,369 discloses the use of cinnamonitrile as a material useful in augmenting or enhancing the aroma of perfume compositions. Cinnamonitrile has the structure:

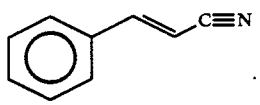

Chem. Abstracts 84:79589 q (Brud, et al) and Arctander, Perfume and Flavor Chemicals (Aroma Chemicals) II, 1969, at Monograph 2597 discloses the use of the compound having the structure:

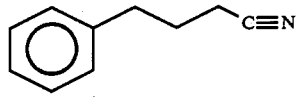

in perfumery.

Nitriles containing methyl moieties "alpha" to the cyanide moiety are disclosed in Blumenthal, et al, U.S. Pat. No. 3,168,550 issued on Feb. 2, 1965.

Nothing in the prior art however discloses any compounds or their uses in perfumery remotely similar to the 1-methyl-1-nitrilo or hydroxylamino-3-(methoxyphenyl)-substituted propanes of our invention.

Furthermore, considerable difficulties have heretofore been encountered in using compounded hypochlorite bleach or sterilizing solutions with perfumed oils so that a stable long-lasting, single phase commercially feasible bleach or sterilizing solution has been difficult to obtain, particularly wherein the desired aroma of the article bleached or sterilized (e.g., clothing) has a pleasant and stable and consistent aroma on drying (and not the usual "hypochlorite-bleached-article" aroma). The problem has been defined in United Kingdom Patent Specification No. 886,084 published on Jan. 3, 1962 wherein it is stated that a stable "dispersion" of hypochlorite-resistant perfume in aqueous solutions of hypochlorites was formulated. United Kingdom Patent Specification No. 886,084 discloses the preparation of an aqueous "solution" of a hypochlorite containing a hypochlorite resistant perfume and a surface active quaternary ammonium compound of the betaine type soluble in the hypochlorite solution. Such ammonium compounds have the generic structure:

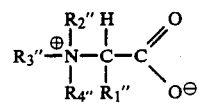

wherein each of $R_1''$, $R_2''$, $R_3''$ and $R_4''$ are alkyl. One of the features of the perfumed solutions produced in accordance with said United Kingdom Patent Specification No. 886,084 is indicated to be that the solution exhibits foaming properties. Another feature of United Kingdom Patent Specification No. 886,084 is stated to be that the perfumed solutions covered by the patent are found to be clear and homogeneous after eight weeks of storage at room temperature. Nevertheless, betaines such as "Ambiteric D" as are discussed therein are not so broadly useful when used in concentrations of from 0.15% up to 4.0% (based on total weight of bleach or sterilizing solution) as to have the ability to be used in conjunction with perfume oils which should be incorporated into thickened, high viscous hypochlorite bleaches or sterilizers having excellent surface tension properties so that long lasting stable soluble single phase thickened perfumed aqueous alkali metal hypochlorite bleach or sterilizing solutions having long lasting pleasant stable aromas are obtained, particularly where the quantity of perfume oil in the bleach or sterilizing substance is at levels of between 0.02% and 0.8% by weight of the total bleach or sterilizing solution. The need for such aromas (e.g., "citrusy") to be present in such bleach or sterilizing solutions exists so that the disagreeable characteristic "hypochlorite" aroma is substantially eliminated from aromas of the product to which the bleach or sterilizing solution is applied; particularly on dry-out, as well as from the aroma of the hands of the user when they are in direct contact with such bleach or sterilizing solutions.

U.S. Pat. No. 3,560,389 also discloses the feasibility of using perfume oils in hypochlorite bleaches or sterilizers at column 3, lines 37-40 but the disclosure is limited to inclusion of various detergents in addition to amine oxides, such as lithium lauryl sulfate and sodium lauryl ether sulfate and/or is further limited to include hydrotropes such as sodium xylene sulfonate in addition to the amine oxide. Exclusion of such hydrotropes and detergents additional to the amine oxides and diphenyl oxide derivatives of our invention is desirable not only to cause the ethyl norbornyl alkyl ethers of our invention to function properly, but also from an ecological standpoint.

European Chemical News, Volume 13, Jan. 18, 1968, sets forth a synopsis of South African Patent No. 67/4667 which corresponds to U.S. Pat. No. 3,560,389, but the reference also states at page 42:

"Alternatively, a detergent with bleaching or bacteriocidal properties can be formulated. Perfuming bleaching solutions is now possible."

Neither the South African nor the United States Patents, however, indicate the advantages and usefulness of limiting the detergents either to (a) compounds having the generic structure:

wherein at least one of $R_1$ and $R_2$ represents $C_{10}$-$C_{12}$ straight chain or branched chain alkyl and when one of $R_1$ or $R_2$ is $C_{10}$-$C_{12}$ branched or straight chain alkyl, the other or $R_1$ or $R_2$ is pH-adjusted hydrogen and wherein $M_\alpha$ and $M_\beta$ are the same or different and each represents alkali metal which may be sodium, lithium or potassium, or (b) to mixtures of compounds having the structure:

with at least one amine oxide defined according to the structure:

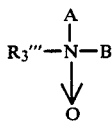

of excluding from the formulation a hydrotrope or of specifying the nature of the perfume oil useful in the perfumed bleach or sterilizing solution (wherein A and B are each separately methyl or taken together, complete a morpholino ring and wherein $R_3'''$ is straight chain alkyl having from 11 up to 13 carbon atoms).

U.S. Pat. No. 3,876,551 in attempting to solve the foregoing problem discloses a stable single phase aqueous alkali metal hypochlorite liquid perfume bleach or sterilizing composition comprising an aqueous mixture of (1) an amine oxide composition consisting essentially of at least one morpholino and/or dimethyl ($C_{11}$-$C_{13}$ straight chain alkyl) amine oxide in an amount greater than 55% of said amine oxide composition, (2) at least one alkali metal hydroxide, (3) at least one alkali metal hypochorite, and (4) a perfume oil compatible with the mixture capable of imparting a "woody" or a "floral" or a "clean fresh" or a "citrusy" note to the bleach or sterilizing composition; the mixture having a pH in the range of from 12 to 13.5 and the mixture excluding hydrotropes as well as all surfactants except the amine oxide. U.S. Pat. No. 3,876,551 also attempts to solve the foregoing problem by disclosing a process for producing the above-named mixture comprising the steps of combining an amide oxide composition consisting essentially of one or more morpholino and/or dimethyl $C_{11}$-$C_{13}$ straight chain alkyl amine oxide(s) with the perfumed oil to form an amine oxide-perfume oil premix; admixing the amine oxide-perfumed oil premix with an aqueous alkali metal hypochlorite solution, and combining an alkali metal hydroxide with the solution whereby the final pH of the mixture is from 12 up to 13.5. In a further effort to solve the foregoing problem U.S. Pat. No. 3,876,551 also discloses adjustment of the pH of the aqueous metal hypochlorite solution initially to the range of 12–13.5 and then combining the resulting aqueous hypochlorite solution with the aforementioned premix. The resulting composition is indicated to cause products to which said composition is applied to have eliminated therefrom the disagreeable characteristics "hypochlorite" aroma and instead to have a "clean fresh" or "floral" or "woody" or "citrusy" aroma to be imparted to the treated products. In addition, it is stated that the hands of the individual user after using and being in direct contact with the hypochlorite composition will not have the disagreeable characteristics "hypochlorite" aroma but instead will have a pleasant "clean fresh" or "floral" or "woody" or "citrusy" aroma.

The disadvantage of the system of U.S. Pat. No. 3,876,551 however, concerns (a) the inability to use a thickener in the system whereby the resulting liquid has a viscosity of 5-25 centipoises at 20°-40° C. and (b) the relatively low degree of chemical stability and substantive stability of the perfume oil and of the single liquid phase system. Nothing in U.S. Pat. No. 3,876,551 indicates such a high degree of stabilities of the perfume-hypochlorite system as exists in the system of the present invention; wherein there is also included a thickener. Indeed, the stabilities using the system of the instant invention are far greater even at levels as low as 3% hypochlorite and are also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the systems taught in the prior art.

Furthermore, nothing in the prior art including the teaching of U.S. Pat. No. 3,876,551 states either explicitly or implicitly the compatability of a thickener in the instant system, such as sodium palmitate, sodium stearate, potassium palmitate, potassium stearate, lithium palmitate, lithium stearate, lithium laurate, potassium laurate or sodium laurate whereby a stable gel (as opposed to a liquid) phase perfumed hypochlorite system or perfumed oil stabilizer emulsifier system "premix" may be produced.

The combination of the compound group having the structure:

(wherein $R_1$, $R_2$, $M_\alpha$ and $M_\beta$ are defined, supra) with perfume and hypochlorite bleach in general, is set forth in the Kao Soap Company, Japanese Patent No.

25514/79 filed on Nov. 2, 1973 and opened for public inspection on Jun. 19, 1975. Thus, on page 2, at column 4, line 15, the compound:

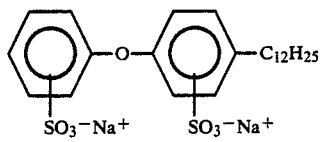

is disclosed for use in conjunction with the perfumed hypochlorite bleaches. The claim of the Kao Soap Patent is as follows:

Claim: An aromatic liquid bleaching composition containing, as active ingredient, sodium hypochlorite, which comprises one or more of simple perfumes or compounded perfumes selected from the group consisting of anisole, benzophenone, benzylphenyl ether, bromelia, cedrenyl acetate, p-tertiary butylcyclohexanol, dimethylbenzylcarbinyl acetate, dihydroterpinyl acetate, diphenyl oxide, dimethylbenzylcarbinol, dimethylphenylcarbinol, dihydroterpineol, fenchyl acetate, fenchyl alcohol, p-methyldimethylbenzylcarbinol, methylphenylcarbinyl acetate, methyl-n-valerate, muskmoskene, muscarone, methylamyl ketone, phenylethyldimethylcarbinyl acetate, rose phenone, styrallyl propionate, tetra hydromuguol, tetra hydromuguyl acetate, tetrahydrolinalool, tetrahydrolinalyl acetate, verool, velveton, verdox, coniferan and yarayara, and a surface active agent which can stably be dissolved in an aqueous solution of sodium hypochlorite.

Furthermore, the use of such compounds as those having the structure:

(wherein $R_1$, $R_2$, $M_\alpha$ and $M_\beta$ have been previously defined) with hypochlorite bleaches is documented in the brochure of Dow Chemical entitled "DOWFAX Surfactants" and is covered in the Dow Chemical Company Patent No. 3,172,861 issued on Mar. 9, 1965.

The 1-methyl-1-nitrilo or hydroxylamino-3-(methoxyphenyl)-substituted propanes of our invention are unique insofar as the aforementioned systems are concerned for use in hypochlorite bleaches. Nothing in the prior art discloses any organic compounds even remotely similar to the 1-methyl-1-nitrilo or hydroxylamino-3-(methoxyphenyl)-substituted propanes of our invention for use as stable aroma augmenting or enhancing agents in hypochlorite bleaches.

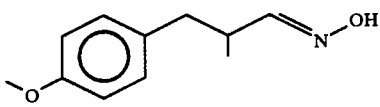

(Conditions: SE-30 column programmed at 220° C. isothermal).

Figure 2:
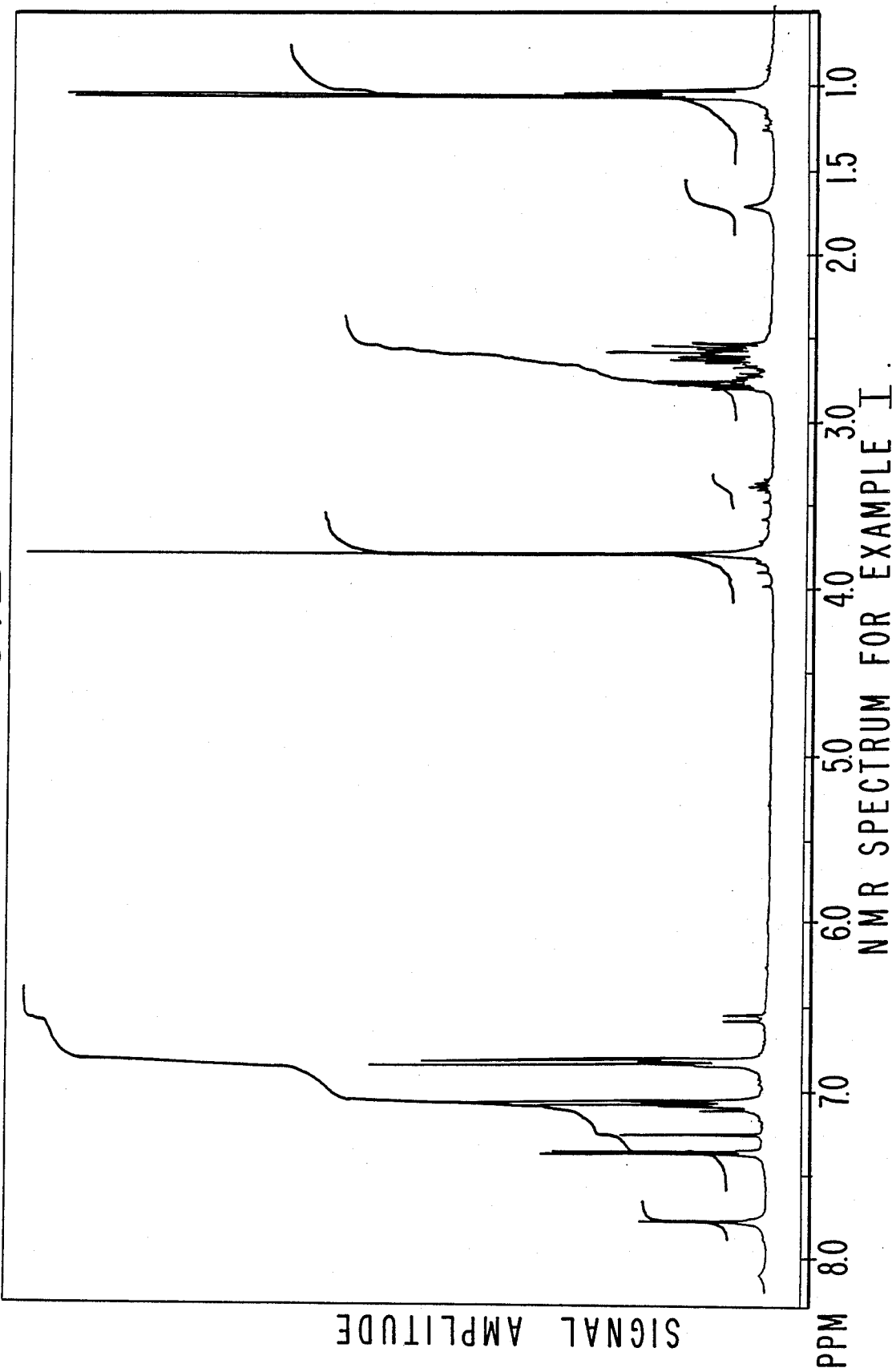

FIG. 2 is the NMR spectrum for the compound having the structure:

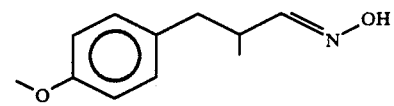

prepared according to Example I.

Figure 3:
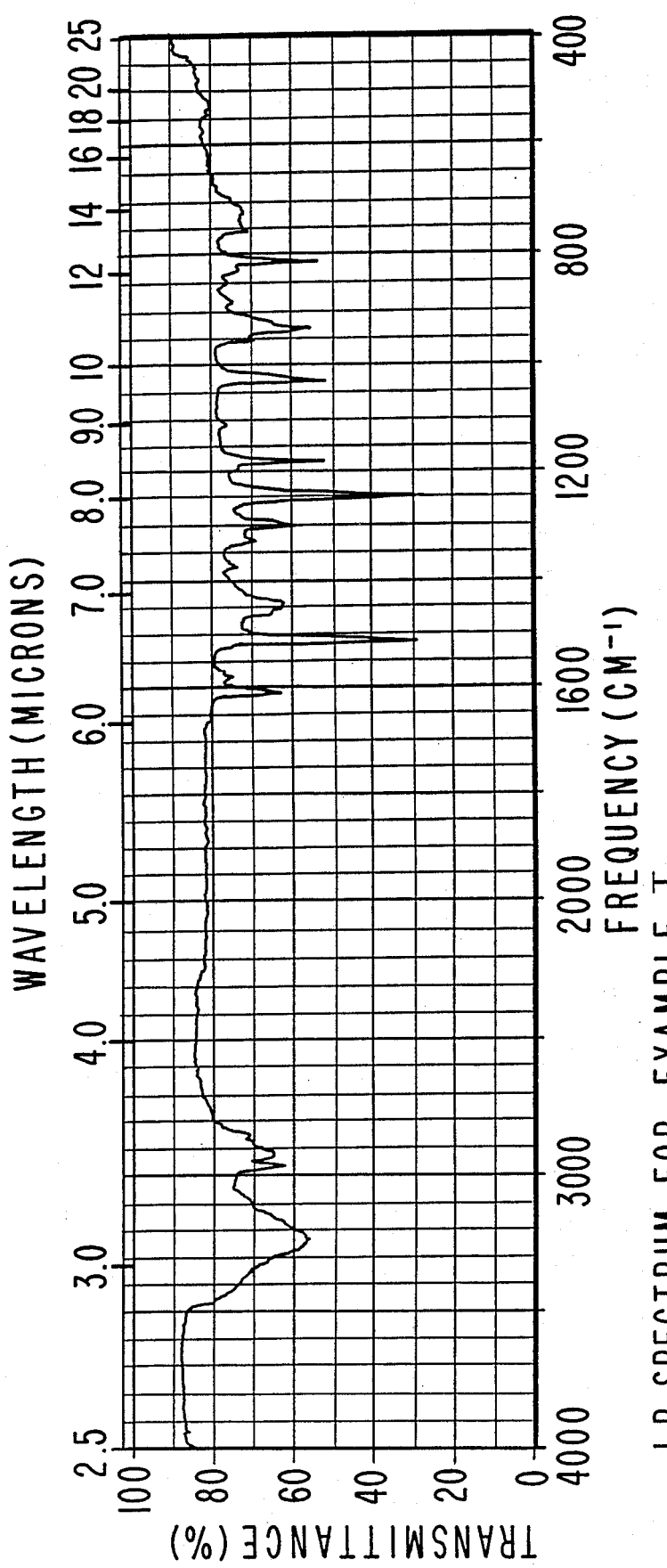

FIG. 3 is the infra-red spectrum for the compound having the structure:

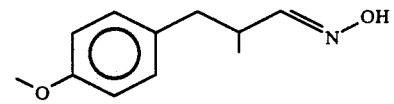

prepared according to Example I.

Figure 4:
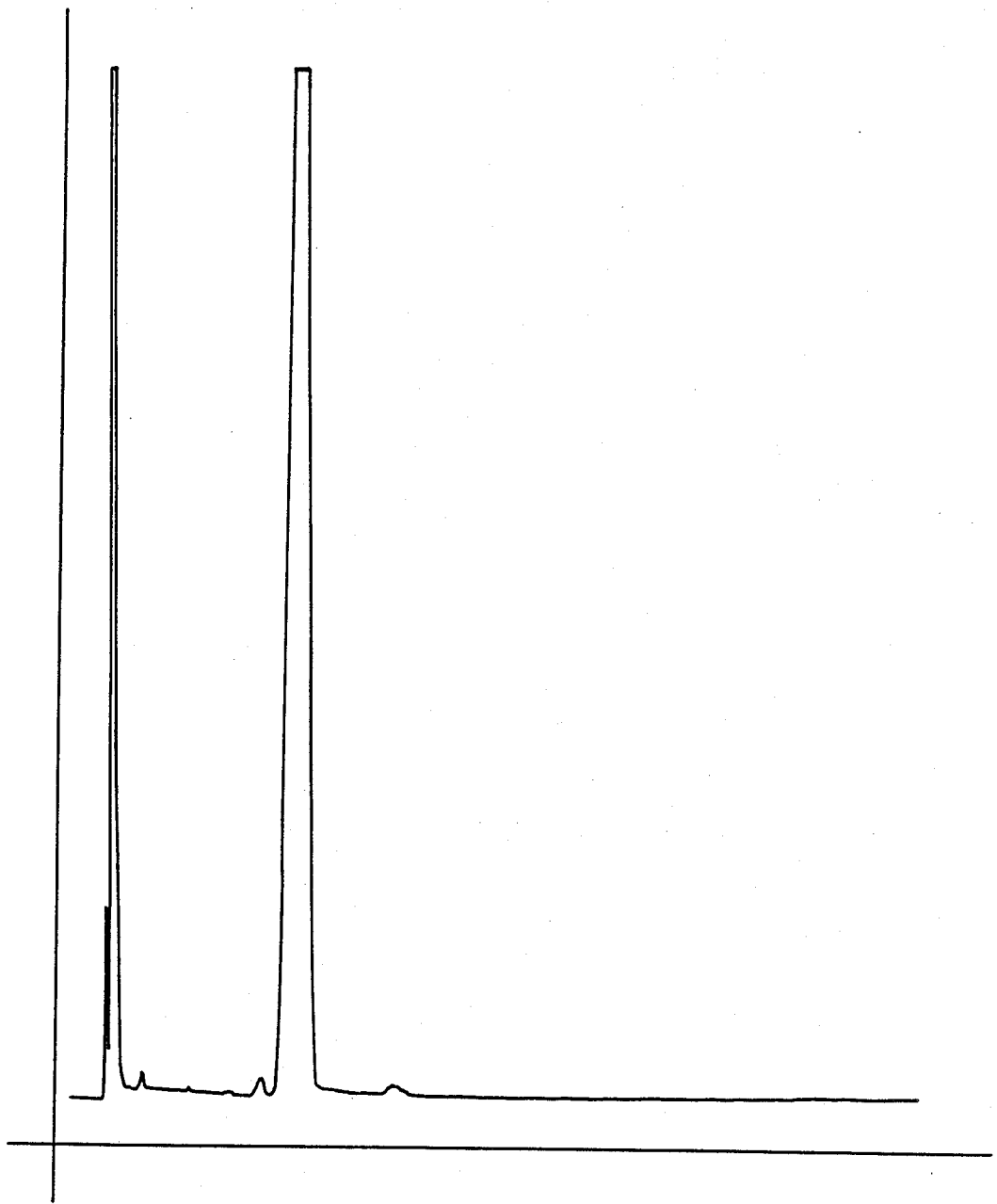

FIG. 4 is the GLC profile for the reaction product of Example II containing the compound having the structure:

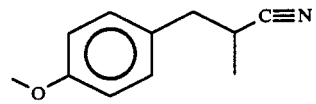

(Conditions: SE-30 column programmed at 220° C. isothermal).

Figure 5:
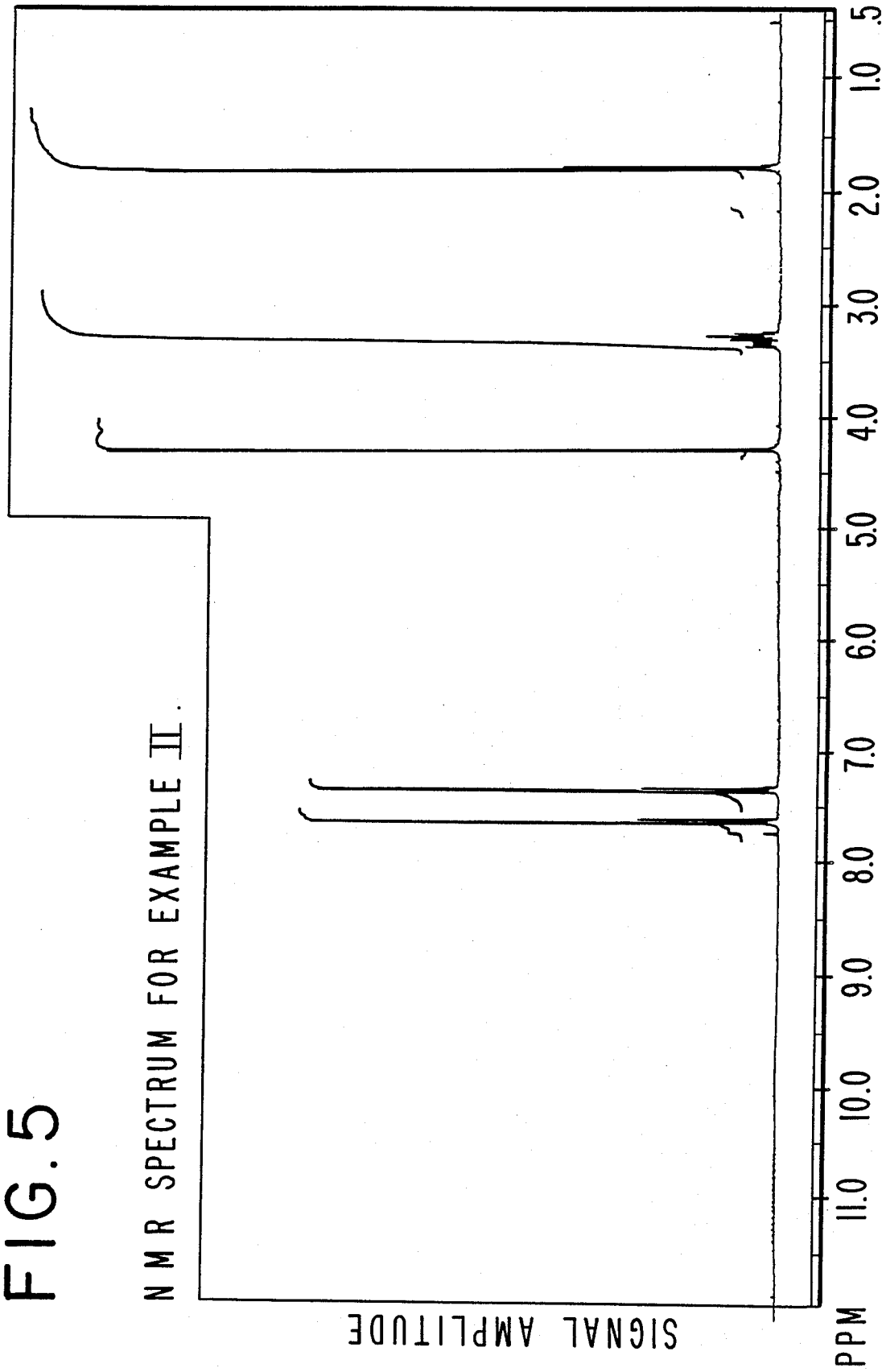

FIG. 5 is the NMR spectrum for the having the structure:

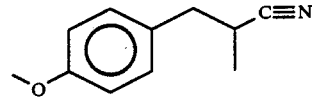

prepared according to Example II.

Figure 6:
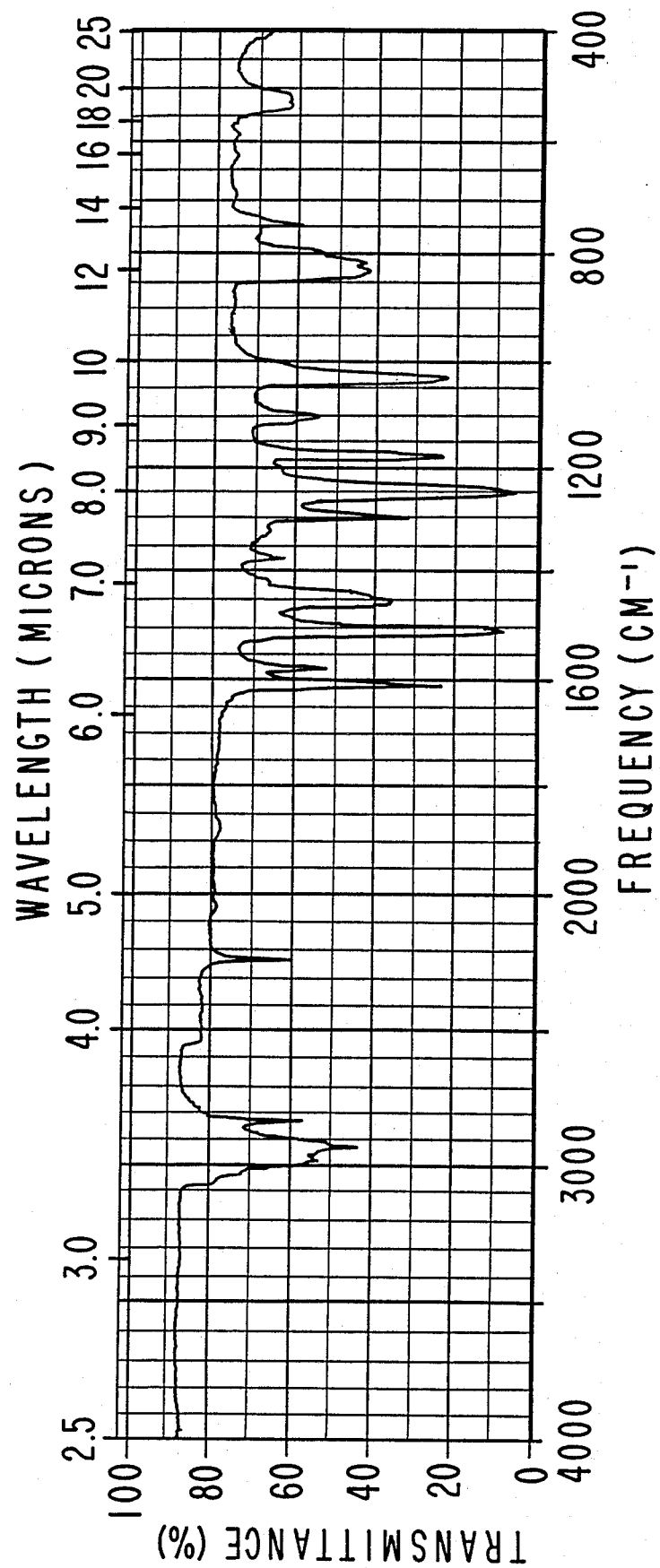

FIG. 6 is the infra-red spectrum for the compound having the structure:

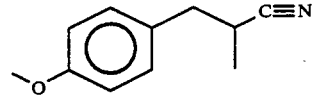

prepared according to Example II.

FIG. 7 represents a cut-away side elevation view of apparatus used in forming perfumed polymers which contain imbedded therein at least one of the 1-methyl-1-nitrilo or hydroxylamino-3-(methoxyphenyl)-substituted propanes of our invention.

FIG. 8 is a front view of the apparatus of FIG. 7 looking in the direction of the arrows.

DETAILED DESCRIPTION OF THE DRAWINGS

Referring to FIGS. 7 and 8, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 7 and 8, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the 1-methyl-1-nitrilo or hydroxylamino-3-(methoxyphenyl)-substituted propanes of our invention or mixtures of 1-methyl-1-nitrilo or hydroxylamino-3-(methoxyphenyl)-substituted propanes of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the 1-methyl-1-nitrilo or hydroxylamino-3-(methoxyphenyl)-substituted propanes of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the 1-methyl-1-nitrilo or hydroxylamino-3-(methoxyphenyl)-substituted propanes of our invention and one or more other substances, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is all of or which contains one or more of the 1-methyl-1-nitrilo or hydroxylamino-3-(methoxyphenyl)-substituted propanes of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides 2-methyl-1-nitrilo- or 2-methyl-1-hydroxylamino-3-(methoxyphenyl) propanes defined according to the generic structure:

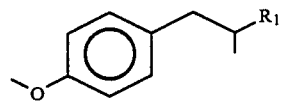

wherein $R_1$ is a nitrogen-containing moiety selected from the group consisting of:

(i) cyanide having the structure:

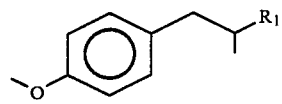

or (ii) hydroxylaminomethyl having the structure:

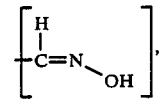

The 1-nitrilo or hydroxylamino-3-(methoxyphenyl)-substituted propanes of our invention produced according to the processes of our invention are capable of augmenting or enhancing sweet, anisic, animalic aromas with sweet and anisic topnotes in perfume compositions, colognes and perfumed articles including soaps, bleaches, anionic, cationic, nonionic or zwitterionic detergents, fabric softener compositions and other perfumed articles.

The 1-nitrilo or hydroxylamino-3-(methoxyphenyl)-substituted propanes of our invention may be produced using as a starting material anisaldehyde having the structure:

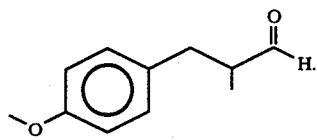

The said anisaldehyde having the structure:

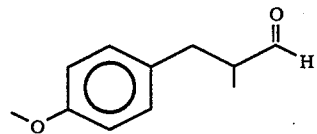

may be reacted with a hydroxylamine salt defined according to the structure:

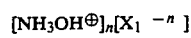

$[NH_3OH^{\oplus}]_n[X_1{}^{-n}]$ in the presence of base according to the reaction:

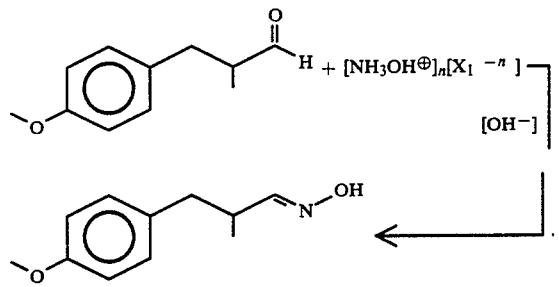

The hydroxylamine salt represented by the structure:

$[NH_3OH^{\oplus}]_n[X_1{}^{-n}]$ may be a sulfate, bisulfate, phosphate, diacid phosphate, monoacid phosphate or sulfite defined, respectively, according to the formulae:

$SO_4{}^=$; $HSO_4{}^-$:

$PO_4{}^{\equiv}$; $H_2PO_4{}^-$:

$HPO_4{}^=$ and $SO_3{}^=$ wherein $X_1$ represents the anion such as sulfate, bisulfate, chloride, bromide, phosphate and the like. The letter n is an integer of from 1 up to 3 and the term "-n" represents the valence of the anion.

The resulting compound having the structure:

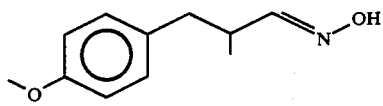

may be fractionally distilled from the reaction mass and used "as-is" for its organoleptic properties.

In the alternative, the resulting compound having the structure:

may be further reacted with a dehydrating agent according to the reaction:

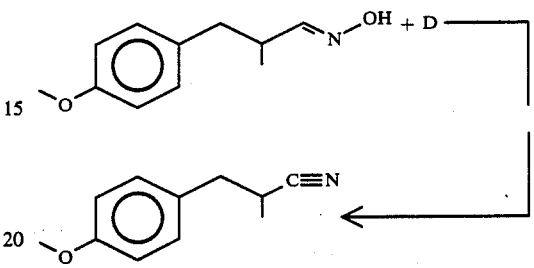

(wherein D represents a dehydrating agent as discussed in more detail, infra) to form the compound having the structure:

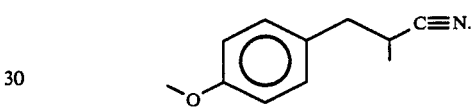

Examples of dehydrating agents useful in this reaction are as follows:
(i) mixtures of copper sulfate and acetic anhydride;
(ii) phosphorous oxychloride;
(iii) phosphorous trichloride;
(iv) phosphorous pentoxide;
(v) thionyl chloride; and
(vi) acetyl chloride.

In the alternative, a methoxy benzylhalide may be reacted with ethyl cyanide directly in the presence of a basic catalyst such as sodamide, potassium hydroxide, diethylamine and the like according to the reaction:

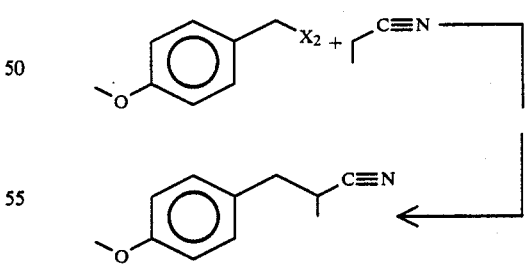

wherein $X_2$ is halogen such as bromo or chloro.

With respect to the reaction:

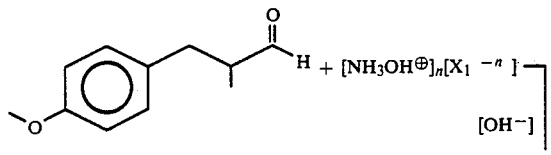

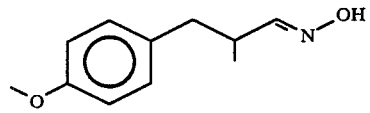

the reaction is carried out at a temperature in the range of from about 50° up to about 70° C. At such a temperature, the reaction time is approximately 1–1.5 hours.

The mole ratio of hydroxylamine salt having the structure:

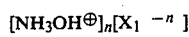

to aldehyde having the structure:

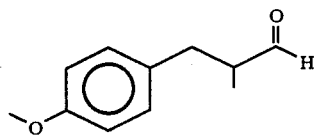

may vary from about 0.5:1.5 up to about 1.5:0.5 with a preferred mole ratio of aldehyde:hydroxylamine salt being about 1.5:1.

At the end of the reaction, the reaction mass is washed with a material such as saturated sodium chloride; solvent extracted; filtered and fractionally distilled.

With reference to the reaction:

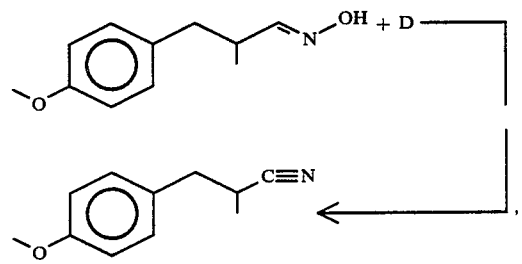

when using the preferred dehydration reagent, the mixture of acetic anhydride and copper sulfate, the reaction preferably takes place at a temperature in the range of from about 100° C. up to about 120° C. over a period of 1.5–2 hours. The preferred mole ratio of acetic anhydride:hydroxylamine derivative defined according to the structure:

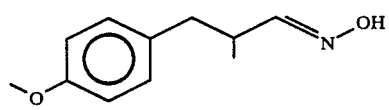

may vary from about 1:1 up to 1.5:1 acetic anhydride:hydroxylamine derivative having the structure:

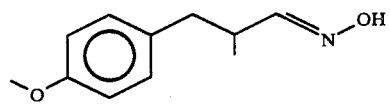

with the quantity of copper sulfate being a catalytic quantity (in an amount of from about 0.2 up to about 0.8% by weight of the reaction mass).

At the end of the reaction, the reaction mass is quenched by adding water dropwise. The resulting product is then washed with weak base, e.g., sodium bicarbonate followed by saturated sodium chloride. The resulting product is then filtered and vacuum distilled to yield product which is organoleptically useful, e.g., in perfumes, perfumed articles and stable perfumed bleaches.

The following table sets forth exemplary reaction products and their organoleptic properties:

TABLE I

| The 1-Methyl-1-Nitrilo Or Hydroxylamino-3-(Methoxyphenyl)-Substituted Propanes: | Organoleptic Properties (Perfumery) |
| --- | --- |
| The compound having the structure: prepared according to Example I. | An anisic aroma with anisic topnotes. |
| The compound having the structure: prepared according to Example II (bulked distillation fractions 10–18). | A sweet, anisic, animalic aroma with sweet, anisic topnotes. |

The 1-methyl-1-nitrilo or hydroxylamino-3-(methoxyphenyl)-substituted propanes of our invention and one or more auxiliary perfume ingredients, including, for example, hydrocarbons, alcohols, ketones, aldehydes, nitriles (other than the nitriles of our invention), esters, lactones, ethers, hydrocarbons, synthetic essential oils and natural essential oils may be admixed so that the combined odors of the individual components produce a pleasant and desired fragrance, particularly and preferably in the "preferably in the hawthorn, new mown hay and lilac" area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characterisitics, however the overall sensory effect of the perfume composition will be at least the sum total of the effects of each of the ingredients. Thus, one or more of the 1-methyl-1-nitrilo or hydroxylamino-3-(methoxyphenyl)-substituted propanes of our invention can be used to alter, modify or enhance the aroma characteristics of a perfume composition, for example, by utilizing or moderating the olfactory reaction contributed by another ingredient in the composition.

The amount of 1-methyl-1-nitrilo or hydroxylamino-3-(methoxyphenyl)-substituted propanes of our invention which will be effective in perfume compositions as well as in perfumed articles and colognes depends upon many factors, including the other ingredients, their amounts and the effects which are desired. It has been found that perfume compositions containing as little as 0.005% of one or more of the 1-methyl-1-nitrilo or hydroxylamino-3-(methoxyphenyl)-substituted propanes of our invention or even less (e.g., 0.002%) can be used to impart sweet, anisic and animalic aromas with sweet and anisic topnotes to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effect desired on the finished product and the particular fragrance sought.

The 1-nitrilo or hydroxylamino-3-(methoxyphenyl)-substituted propanes of our invention are useful (taken alone or together with other ingredients in perfume compositions), in detergents and soaps, space odorants and deodorants, perfumes, colognes, toilet water, bath preparations such as lacquers, brilliantines, pomades and shampoos; cosmetic preparations such as creams, deodorants, hand lotions and sun screens; powders, such as talcs, dusting powders, face powders and the like. As little as 0.7% of the 1-nitrilo or hydroxylamino-3-(alkyl phenyl)-substituted propanes of our invention will suffice to impart an intense and substantive sweet, anisic and animalic aromas with sweet and anisic topnotes to hawthorn, cassie, new mown hay and lilac perfume formulations. Generally, no more than 5% of the 1-nitrilo or hydroxylamino-3-(methoxyphenyl)-substituted propanes of our invention based on the ultimate end product is required to be used "as is" or in the perfume composition.

Furthermore, as little as 0.25% of one or more of the 1-nitrilo or hydroxylamino-3-(methoxyphenyl)-substituted propanes of our invention will suffice to impart such aroma to perfumed articles per se, whether in the presence of other perfume materials or whether used by themselves. Thus, the range of use of the 1-methyl-1-nitrilo or hydroxylamino-3-(methoxyphenyl)-substituted propanes of our invention in perfumed articles may vary from about 0.25% up to about 5% by weight based on the total weight of the perfumed article.

In addition, the perfume composition or fragrance composition of our invention can contain a vehicle, or carrier for the 1-methyl-1-nitrilo or hydroxylamino-3-(methoxyphenyl)-substituted propanes of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition by means of coacervation (such as gelatin).

It will thus be apparent that the 1-methyl-1-nitrilo or hydroxylamino-3-(methoxyphenyl)-substituted propanes of our invention can be utilized to alter, modify or enhance the aroma of perfume compositions, colognes or perfumed articles.

Furthermore, several processes may be used in order to produce a thickened, highly viscous hypochlorite bleaching or sterilizing solution whereby the desired aroma profiles are imparted to the articles treated with said hypochlorite solutions.

Thus, for example, the 1-methyl-1-nitrilo or hydroxylamino-3-(methoxyphenyl)-substituted propanes of our invention may be premixed with the diphenyl oxide derivative or diphenyl oxide derivative-amine oxide solubilizer-stabilizer (having the structures, respectively:

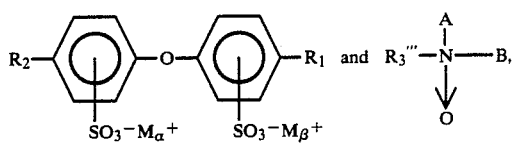

and the resulting 1-methyl-1-nitrilo or hydroxylamino-3-(methoxyphenyl)-substituted propanes of our invention or 1-methyl-1-nitrilo or hydroxylamino-3-(methoxyphenyl)-substituted propanes premix is then mixed with the hypochlorite bleaching or sterilizing solution with stirring. Immediately after such addition, an aqueous alkali metal hydroxide solution is added to the mixture to bring the pH to the range of 11–14.0. A pH of less than 11 is not desired since it is difficult to achieve a single phase stable system at low pH's. A pH higher than 14.0 will also create a system which (1) is unnecessarily corrosive; (2) will narrow the range of perfume oils useable (in conjunction with the 1-methyl-1-nitrilo or hydroxylamino-3-(methoxyphenyl)-substituted propanes) of the system and (3) will limit the particular ingredients useable in such perfume oils in conjunction with the 1-methyl-1-nitrilo or hydroxylamino-3-(methoxyphenyl)-substituted propanes. On the other hand, if for example, the 1-methyl-1-nitrilo or hydroxylamino-3-(methoxyphenyl)-substituted propanes is used alone or further in combination with (i) diisoamylene epoxides; (ii) diisoamylenes as described in application for U.S. Ser. No. 188,576 filed on Oct. 9, 1980; now U.S. Pat. No. 4,303,555 issued on Dec. 1, 1981 or (iii) acyl diisoamylene derivatives described in application for U.S. Ser. No. 185,132 filed on Sept. 4, 1980, now U.S. Pat. No. 4,321,255 issued on Mar. 23, 1982 and/or (iv) ketal derivatives of acyl diisoamylene derivatives described in application for U.S. Ser. No. 212,993 filed on Dec. 4, 1980, now U.S. Pat. No. 4,315,952 issued on Feb. 16, 1982, a pH of about 14.0 and even slightly higher (e.g., 14.1) is acceptable.

The aqueous alkali metal hydroxide can be added to the aqueous alkali metal hypochlorite solution before adding the diphenyl oxide derivatives (taken alone or in conjunction with the amine oxide) or the 1-methyl-1-nitrilo or hydroxylamino-3-(methoxyphenyl)-substituted propanes or mixtures of 1-methyl-1-nitrilo or hydroxylamino-3-(methoxyphenyl)-substituted propanes or mixtures of 1-methyl-1-nitrilo or hydroxylamino-3-(methoxyphenyl)-substitued propanes with other materials such as diisoamylene epoxides. Indeed, the ingredients: the 1-methyl-1-nitrilo or hydroxylamino-3-(methoxyphenyl)-substituted propanes; the alkali metal hydroxide and the diphenyl oxide derivative or diphenyl oxide derivative-amine oxide composition (having the structures, respectively

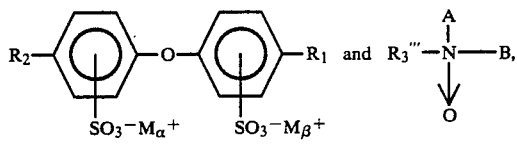

may be added or admixed in any order which is convenient to the formulator.

The alkali metal hypochlorites preferred in the practice of our invention are: sodium hypochlorite, potassium hypochlorite and lithium hypochlorite or mixtures of same. The alkali metal hypochlorites preferred in the practice of this invention are: lithium hydroxide, potassium hydroxide and sodium hydroxide, or, if desired, mixtures of such hydroxides.

The temperature at which the composition of our invention remains both substantially stable and commercially useful for the purposes set forth herein (that is, remains as a clear single aqueous or gel phase) and retains (1) the desired properties inherent in the known bleaching and sterilizing uses of aqueous alkali metal hypochlorite liquid or gel solutions, and (2) the properties imparted thereto as a result of the use of the 1-methyl-1-nitrilo or hydroxylamino-3-(methoxyphenyl)-substituted propanes which impart to articles previously subjected to the aqueous alkali metal hypochlorite gel or liquid solutions a desired aroma profile, varies from approximately 20° F. up to approximately 120° F. At temperatures below 20° F. a two-phase system usually occurs and at temperatures higher than 120° F. the bleaching or sterilizing efficiency of the compositions of our invention is diminished at an excessive rate.

When it is desired to (1) initially form the $C_{10}$-$C_{12}$ straight chain or branched chain diphenyl oxide alkali metal sulfonate or diphenyl oxide derivative-amine oxide premix; (2) then combine the resulting premix with an alkali metal hypochlorite solution; (3) then add the thickening agent and then (4) adjust the pH of the resulting solution to the range of 11–14.0, then the temperature of mixing ranges which are considered to be within the scope of this invention are as follows:

| | | |
|---|---|---|
| (a) | Formation of the diphenyl oxide derivative or diphenyl oxide-amine oxide-1-methyl-1-nitrilo or hydroxylamino-3-(methoxyphenyl)-substituted propanes premix | 20° F.–150° F. |
| (b) | Mixing the premix with aqueous alkali metal hypochlorite solution followed by thickening agent | 20° F.–120° F. |
| (c) | Adjustment of pH of the solution to the range of 11–14.0 using aqueous alkali metal hydroxide solution | 20° F.–120° F. |

In any event, whenever a mixing unit operation involves the aqueous alkali metal hypochlorite solution, the temperature of mixing is limited to the range of 20° F.–120° F. Where the mixing unit operation involves the mixing of 1-methyl-1-nitrilo or hydroxylamino-3-(methoxyphenyl)-substituted propanes, the upper bound of the temperature range is limited by the stability of the 1-methyl-1-nitrilo or hydroxylamino-3-(methoxyphenyl)-substituted propanes or other perfume ingredient mixed with the 1-methyl-1-nitrilo or hydroxylamino-3-(methoxyphenyl)-substituted propanes useable in the practice of our invention; and the lower bound of said temperature range is limited by the least temperature where a single liquid phase or gel phase including the 1-methyl-1-nitrilo or hydroxylamino-3-(methoxyphenyl)-substituted propanes or other ingredients admixed therewith will exist. Where a unit mixing operation of the process of our invention involves the mixing of one or more diphenyl oxide derivatives having the generic structure:

taken alone or taken together with one or more amine oxides having the generic structure:

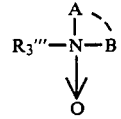

with other materials, the upper bound of the temperature range is the decomposition point of any one of the diphenyl oxide derivatives or amine oxide components and the lower bound is the least temperature where a single liquid phase or gel phase, including the diphenyl oxide derivatives or diphenyl oxide-amine oxide mixture will exist.

Preferred diphenyl oxide derivative compositions from a practical standpoint useful in the practice of our invention are compounds having the structure:

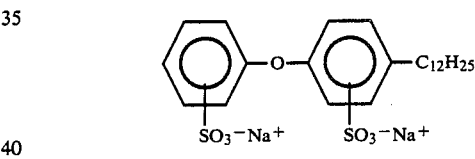

where th $C_{12}H_{25}$ moiety represents one or a series of different branched chains; compounds defined according to the structure:

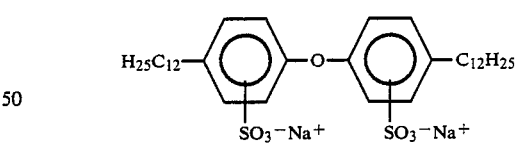

where the $C_{12}H_{25}$ moiety represents one or a series of different branched chains; compounds defined according to the structure:

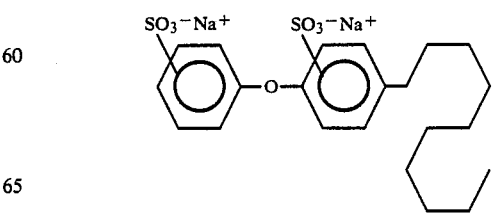

and compounds defined according to the structure:

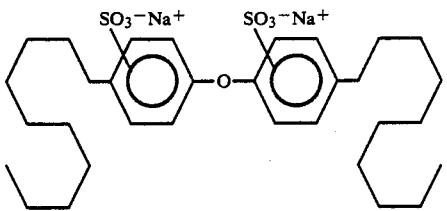

otherwise known as DOWFAX® 2A1 in the case where one or $R_1$ or $R_2$ represents branched $C_{12}H_{25}$ alkyl chains and the other of $R_1$ or $R_2$ represents hydrogen, or DOWFAX® 3B2 in the case where one of $R_1$ or $R_2$ represents straight $C_{10}$ alkyl chain and the other of $R_1$ or $R_2$ represents hydrogen (DOWFAX® being a registered trademark of the Dow Chemical Company of Midland, Michigan).

When used in conjunction with the diphenyl oxide derivatives preferred amine oxide compositions, from a practical standpoint, useful in the practice of our invention are the commercially available (1) dimethyl "cocoamine" oxide (a mixture which is dominated by dimethyl-$C_{12}$-$C_{16}$ straight chain alkyl amine oxides; more particularly a mixture containing approximately 70% $C_{12}$ straight chain alkyl amines oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$-$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: AROMOX® DMC-W and AROMOX® DMMC-W which are 30% aqueous dimethyl cocoamine oxide solutions and AROMOX® NCMDW which is a 40% aqueous N-cocomorpholine oxide solution each of which is produced by the Armac Division of AKZO of Chicago, Ill. These materials are described in Brochure 68011, published by Armour Industrial Chemicals, P.O. Box 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine-oxide 1-methyl-1-nitrilo or hydroxylamino-3-(methoxyphenyl)-substituted propanes compositions covered by our invention. The usual percent of alkali metal hypochlorite in solution is about 5%, the percentage of sodium hypochlorite in such mixtures as CLOROX® the registered trademark of the Clorox Corporation.

The perfume oil used in conjunction with the 1-methyl-1-nitrilo or hydroxylamino-3-(methoxyphenyl)-substituted propanes which, in turn, is used in conjunction with the aqueous alkali metal hypochlorite solution must have such properties as to be able (1) to be compatible with the 1-methyl-1-nitrilo or hydroxylamino-3-(methoxyphenyl)-substituted propanes; (2) to impart to the resulting or "aqueous alkali metal hypochlorite" liquid or gel solution a pleasant aroma which harmonizes with the aroma of the 1-methyl-1-nitrilo or hydroxylamino-3-(methoxyphenyl)-substituted propanes; (3) to effect a substantial diminution or elimination of the disagreeable "hypochlorite" aroma which is imparted to surfaces (e.g., bleached laundry or the hands of the user which are in direct contact with the hypochlorite solution) on which known aqueous alkali metal hypochlorite solutions have been used; and (4) to impart to the surfaces with which such aqueous alkali metal hypochlorite solutions are in contact, a pleasant long lasting stable aroma. Examples of ingredients compatible with 1-methyl-1-nitrilo or hydroxylamino-3-(methoxyphenyl)-substituted propanes and suitable for the aforementioned purposes, that is, useable in conjunction with the hypochlorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. Nos. 3,360,530 and 3,591,528 such as 6-oxa-1,1,3,3,8-pentamethyl-2,3,5,6,7,8-hexahydro-1H-benz(f) indene;
3. Polycyclic ethers covered by U.S. Pat. No. 3,281,432, such as octahydro-1,3a, 6-trimethyl-1H-1,6a, ethanopentaleno-(1,2-C)furan;
4. Polycyclic ketones such as hexahydro-1,1,5,5-tetramethyl-2H-2,4a-methanonaphthalen-8-(5H)one;
5. Diisoamylenes described according to application for U.S. Ser. No. 188,576 filed on Sept. 18, 1980;
6. Acyl diisoamylene derivatives described according to application for U.S. Ser. No. 184,132 filed on Sept. 4, 1980 and ketal derivatives thereof described according to application for U.S. Ser. No. 212,993 filed on Dec. 4, 1980; and
7. Diisoamylene epoxide derivatives prepared according to application for U.S. Ser. No. 231,773 filed on Feb. 27, 1981.

It will be understood that a number of materials which impart to the sweet, anisic and animalic aroma of 1-methyl-1-nitrilo or hydroxylamino-3-(methoxyphenyl)-substituted propanes of our invention additional eucalyptol-like, or minty or woody nuances will not be useful for our invention because they are, inter-alia, easily oxidized by the alkali metal hypochlorite in the system. Examples are 1,5,9-trimethyl-12-acetyl-cyclo- dodecatriene-1,5,8 and 1,5,9-trimethyl-12-cyclododecadiene-1,8 covered by British Patent No. 1,204,409.

A basic feature of our invention concerns the fact that the only detergent group needed or desirable in the composition of our invention is the class of diphenyl oxide derivatives defined according to the structure:

wherein $R_1$, $R_2$, $M_\alpha$ and $M_\beta$ are defined, supra, taken alone or in conjunction with the class of morpholino and/or dimethyl $C_{11}$-$C_{13}$ straight chain alkyl amine oxides defined according to the structure:

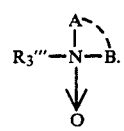

More specifically, such detergents as sodium decyl ether sulfate, sodium myristyl ether sulfate, sodium lauryl ether sulfate and lithium lauryl ether sulfate are neither desired nor are they required. Furthermore, the well known hydrotropes employed in prior art compositions such as the well known family of clarifying agents comprising the alkali metal or alkali earth metal salts of mono- and polyalkylated benzene or naphthalene sulfonates such as sodium xylene or magnesium toluene sulfonate are again neither desired nor are they required in the compositions intended to be encompassed by the instant invention.

Another basic feature of our invention concerns the fact that when it is desired to have a gel phase composition, thickener agents may be employed in conjunction with the system; hypochlorite bleach-1-methyl-1-nitrilo or hydroxylamino-3-(methoxyphenyl)-substituted propanes-diphenyl oxide derivative or diphenyl oxide derivative-amine oxide derivative (having the general structure and having the structure:

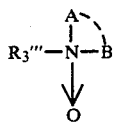

of our invention).

Still another basic feature of our invention concerns the fact that the gel phase compositions including thickener agents are empolyed with the "premix" system: 1-methyl-1-nitrilo or hydroxylamino-3-(methoxyphenyl)-substituted propanes-diphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being in a semi-solid state, is unobviously, advantageously and unexpectedly stable over long periods of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on the overall weight of hypochlorite bleach-diphenyl oxide derivative (or diphenyl oxide derivative-amine oxide)-1-methyl-1-nitrilo or hydroxylamino-3-(methoxyphenyl)-substituted propanes composition of our invention. When it is merely desired to have a thickened "premix" the percentage of thickening agent may vary from about 5% up to about 40% by weight of thickener based on overall weight of "premix".

The following Examples I and II serve to illustrate processes for producing the 1-methyl-1-nitrilo or hydroxylamino-3-(methoxyphenyl)-substituted propanes of our invention. Examples following Example II in general serve to illustrate organoleptic utilities of the 1-methyl-1-nitrilo or hydroxylamino-3-(methoxyphenyl)-substituted propanes of our invention.

In general, the following examples serve to illustrate specific embodiments of our invention. It will be understood that these examples are illustrative and that the invention is to be considered restricted thereto only as indicated in the appended claims.

All parts and percentages given herewith are by weight unless otherwise specified.

EXAMPLE I

Preparation of Canthoxal Oxime

Reaction:

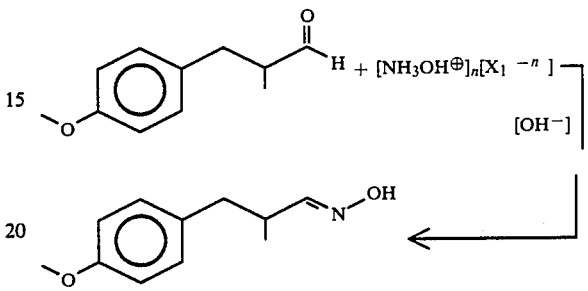

(wherein X is SO$_4$= and wherein n is 2).

Into a 5 liter reaction vessel equipped with stirrer, thermometer, heating mantle and addition funnel is placed 1500 ml water and 707 grams (4.3 moles) of hydroxylamine sulfate.

The hydroxylamine sulfate-water mixture is stirred until homogeneous while maintaining the temperature at 15° C. Over a period of 5 minutes while stirring the reaction mass and maintaining same at a temperature of 15° C., 1068 grams (6 moles) of the aldehyde having the structure:

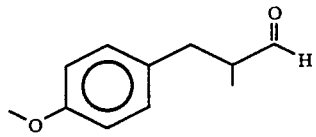

is added to the reaction mass.

791 Grams (9.89 moles) of sodium hydroxide in a 50% aqueous solution is then added to the reaction mass over a period of 1.5 hours while maintaining the reaction temperature in the range of 50°-57° C.

The reaction mass is then aged at 55° C. for a period of two hours.

The reaction mass is then allowed to cool to 40° C. and the organic phase (product) precipitates as a solid. The solid is filtered and rinsed with three 1000 ml portions of water. The white filter cake is dissolved in methyl alcohol and refrigerated overnight. Crystals of the compound having the structure:

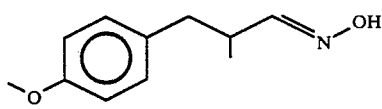

(650 grams) are then filtered from the product. The mother liquor is concentrated thereby causing additional compound having the structure:

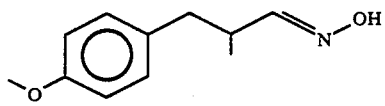

to precipitate the recrystallization of the second crop of crystals gives rise to 325 grams. The overall yield is 84%.

The resulting product has an intense and long-lasting anisic aroma with anisic topnotes.

Figure 1:
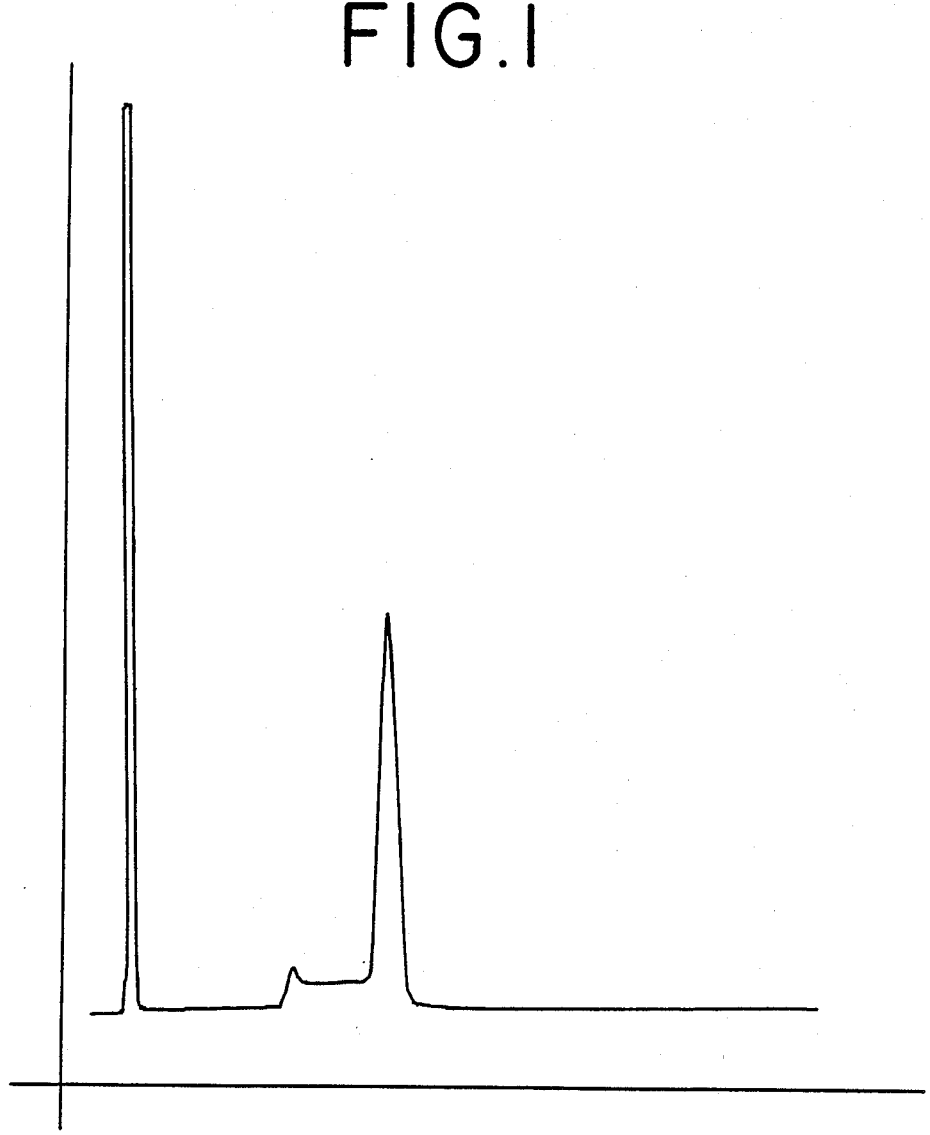
FIG. 1 is the GLC profile of the crude reaction product of Example I containing the compound defined according to the structure.

FIG. 1 is the GLC profile for the reaction product prior to filtration.

FIG. 2 is the NMR spectrum for the compound having the structure:

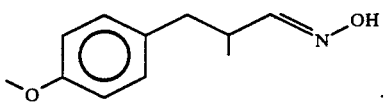

FIG. 3 is the infra-red spectrum for the compound having the structure:

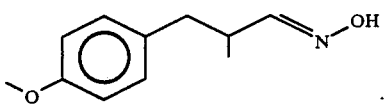

EXAMPLE II

Preparation of Canthoxal Nitrile

Reaction:

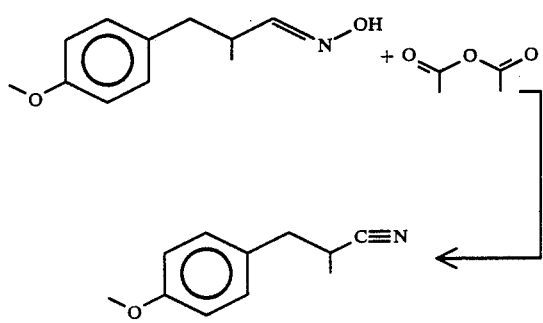

Into a 5 liter reaction flask equipped with thermometer, stirrer, reflux condenser and heating mantle are placed 917 grams of acetic anhydride (9 moles) and 8.1 grams of copper sulfate. The resulting mixture is heated to 100° C. with stirring.

Over a 1.5 hour period while maintaining the reaction temperature at 98°–100° C., 975 grams of the compound having the structure:

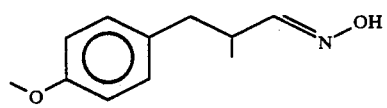

is added to the reaction mass in 10 gram portions.

The reaction mass is then aged with stirring for a period of 0.5 hours. The reaction mass is then quenched by means of the addition of 1 liter of water while maintaining the reaction mass temperature at 100° C. The reaction mass is then let stand overnight at room temperature. The reaction mass now exists in two phases; an aqueous phase and an organic phase. The organic phase is washed with 1000 ml water followed by two 400 ml portions of sodium bicarbonate solution (saturated) followed by two 500 ml portions of saturated sodium chloride solution.

The resulting product is filtered through anhydrous magnesium sulfate and fractionally distilled to yield the following fractions:

| Fraction No. | Vapor Temp. (°C.) | Liquid Temp. (°C.) | Vacuum mm/Hg. Pressure |
|---|---|---|---|
| 1 | 85/126 | 131/139 | 1.87/2.43 |
| 2 | 128 | 135 | 2.55 |
| 3 | 127 | 135 | 2.35 |
| 4 | 125 | 136 | 1.88 |
| 5 | 125 | 138 | 1.88 |
| 6 | 125 | 139 | 1.88 |
| 7 | 127 | 138 | 1.92 |
| 8 | 128 | 138 | 1.99 |
| 9 | 130 | 138 | 2.14 |
| 10 | 130 | 140 | 2.12 |
| 11 | 130 | 140 | 2.12 |
| 12 | 130 | 141 | 2.12 |
| 13 | 130 | 141 | 2.12 |
| 14 | 130 | 144 | 2.09 |
| 15 | 130 | 144 | 2.10 |
| 16 | 130 | 144 | 2.10 |
| 17 | 132 | 145 | 2.20 |
| 18 | 132 | 145 | 2.23 |
| 19 | 134 | 159 | 2.39 |
| 20 | 132 | 200 | 2.42. |

Distillation fractions 10–18 are bulked. Bulked distillation fractions 10–18 have a sweet, anisic, animalic aroma with sweet and anisic topnotes.

FIG. 4 is the GLC profile for the reaction product prior to distillation (Conditions: SE-30 column programmed at 220° C. isothermal).

FIG. 5 is the NMR spectrum for the compound having the structure:

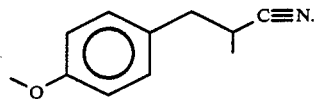

FIG. 6 is the infra-red spectrum for the compound having the structure:

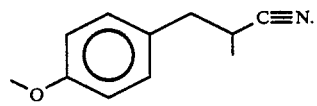

EXAMPLE III

The following Acacia soap perfume formulations are prepared:

| Ingredients | Parts by Weight | |
|---|---|---|
| | III(A) | III(B) |
| Acetophenone | 50 | 50 |
| Bergamot oil | 100 | 100 |
| Geranium oil - Algerian | 200 | 200 |
| β-Ionone | 50 | 50 |
| Bromstyrole | 20 | 20 |

-continued

| Ingredients | Parts by Weight | |
|---|---|---|
| | III(A) | III(B) |
| α-Terpineol | 100 | 100 |
| Nerol | 30 | 30 |
| Vetiver oil - Venezuela | 20 | 20 |
| Styrax | 10 | 10 |
| Musk Xylene | 60 | 60 |
| Hydrocinnamic aldehyde | 10 | 10 |
| The compound having the structure: | 52 | 0 |

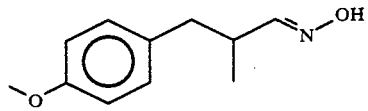

prepared according to Example I.

| The compound having the structure: | 0 | 52 |

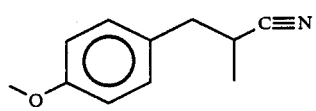

prepared according to Example II (bulked distillation fractions 10-18.

The resulting Acacia soap perfume of Example III(A) has an acacia, cassie and new mown hay aroma with anisic understones and anisic topnotes, said anisic undertones and anisic topnotes being present as a result of the use of the compound having the structure:

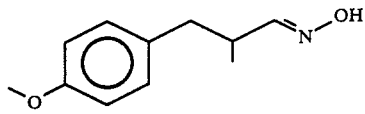

The resulting perfume formulation of Example III(B) has an acacia, cassie and new mown hay aroma with sweet, anisic topnotes and sweet, anisic and animalic undertones. The sweet, anisic topnotes and the sweet, anisic and animalic undertones are present in the formulation as a result of the addition of the compound having the structure:

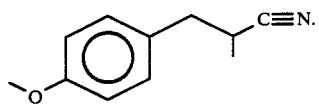

EXAMPLE IV

Preparation of Cosmetic Powder Compostiions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 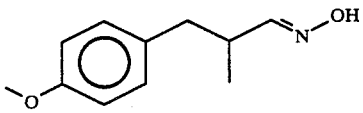 prepared according to Example I. | An anisic aroma with anisic topnotes. |
| The compound having the structure: 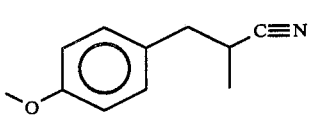 prepared according to Example II, bulked distillation fractions 10–18. | A sweet, anisic, animalic aroma with sweet, anisic topnotes. |
| Perfume composition of Example III(A). | Acacia, cassie and new mown hay aroma with anisic undertones and anisic topnotes. |
| Perfume composition of Example III(B). | Acacia, cassie and new mown hay aroma with sweet, anisic topnotes and sweet, anisic and animalic undertones. |

EXAMPLE V

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substance as set forth in Table II of Example IV.

EXAMPLE VI

Preparation of Colognes and Handkerchief Perfumes

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII

Preparation of Soap Compositions

One hundred grams of soap chips [per sample] (IVORY ®, produced by the Procter & Gamble Company of Cincinnati, Oh.), are each mixed with one gram samples of substances as set forth in Table II of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example IV.

EXAMPLE VIII

Preparation of Solid Detergent Compositions

Detergents are prepared using the following ingredients according to Example I of Canadian Patent No. 1,007,948:

| Ingredient | Percent by Weight |
|---|---|
| "NEODOL ® 45-11 (a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating and the perfuming material are as follows:
 1. A water "dissolvable" paper ("Dissolvo Paper");
 2. Adogen 448 (m.p. about 140° F.) as the substrate coating; and
 3. An outer coating having the following formulation (m.p. about 150° F.):
   57% - $C_{20-22}$ HAPS
   22% - isopropyl alcohol
   20% - antistatic agent
   1% - of one of the substances as set forth in Table II of Example IV.

Fabric softening compositions prepared according to Example I at column 15 of U.S. Pat. No. 3,632,396 having aroma characteristics as set forth in Table II of Example IV, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example IV.

EXAMPLE X

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example IV. | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Oh.); 1.0 weight percent ethylene glycol distearate (prepared by the Armak Corporation) and triethanolamine (a product of Union Carbide Corporation) (1.4 weight percent). The resulting melt is admixed with Stephanol WAT produced by the Stepan Chemical Company (35.0 weight percent). The resulting mixture is heated to 60° C. and mixed until a clear solution is obtained (at 60° C.).

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

EXAMPLE XII

Four drops of each of the substances set forth in Table II of Example IV, supra, is added separately to two grams of AROMOX ® DMC-W to produce a clear premix. The clear premix is added to 200 grams of CLOROX ® with stirring resulting in a clear stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example IV. Furthermore, no such characteristic "hypochlorite" aroma is retained on the hands of the individual handling such laundry in both the wet and the dry states.

EXAMPLE XIII

AROMOX ® DMMC-W in various quantities is mixed with 0.1 grams of one of the substances set forth in Table II of Example IV, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table II of Example IV. Furthermore, no such characteristic "hypochlorite" aroma is retained on the hands of the individual handling such laundry in both the wet and dry states.

EXAMPLE XIV

Two grams of AROMOX ® DMMC-W is admixed with eight drops of one of the substances set forth in Table II of Example IV, supra. The premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry, on dry-out in an atmosphere of 50% relative humidity retains a "clean" warm aroma as set forth in Table II of Example IV, supra; whereas without the use of the substance set forth in Table II of Example IV, supra, the bleached laundry has a faint characteristic disagreeable "hypochlorite" aroma.

EXAMPLE XV

Two grams of AROMOX ® DMMC-W is admixed with eight drops of one of the substances of Table II of Example IV, supra. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table II of Example IV, supra; whereas without the use of the substance set forth in Table II of Example IV, supra, the bleached laundry has a faint characteristic disagreeable "hypochlorite" aroma.

EXAMPLE XVI

Two grams of AROMOX ® DMMC-W is admixed with eight drops of one of the substances as set forth in Table II of Example IV, supra. This premix is then added with stirring to 200 grams of a mixture containing 4.5% aqueous sodium hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table II of Example IV, supra, whereas without the use of the substance set forth in Table II of Example IV, supra, the bleached laundry has a faint characteristic disagreeable "hypochlorite" aroma.

EXAMPLE XVII

Four drops of one of the substances set forth in Table II of Example IV, supra, is added to 1.5 grams of AROMOX ® to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table II of Example IV, supra. Furthermore, no such characteristic "hypochlorite" aroma is retained on the hands of the individual handling such laundry in both the wet and dry states.

EXAMPLE XVIII

Four drops of one of the substances set forth in Table II of Example IV, supra, is added to 1 gram n-undecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table II of Example IV, supra. Furthermore, no such characteristic "hypochlorite" aroma is retained on the hands of the individual handling such laundry in both the wet and the dry states.

EXAMPLE XIX

Four drops of one of the substances as set forth in Table II of Example IV, supra are added to 1 gram of n-dododecyl dimethyl amine oxide to produce a clear premix. The clear premix is added to 200 grams of CLOROX ® with stirring resulting in a clear, stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table II of Example IV, supra. Furthermore, no such characteristic "hypochlorite" aroma is retained on the hands of the individual handling such laundry in both the wet and dry states.

EXAMPLE XX

One gram of n-tridecyl dimethyl amine oxide is admixed with eight drops of one of the substances as set forth in Table II of Example IV, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table II of Example IV, supra, whereas without the use of one of the substances of Table II of Example IV, supra, the bleached laundry has a faint characteristic disagreeable "hypochlorite" aroma.

EXAMPLE XXI

Four drops of the compound having the structure:

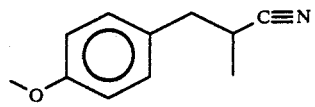

prepared according to Example II (bulked fractions 10–18) is added to 2 grams of AROMOX ® DMC-W to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a sweet, anisic and animalic aroma. Furthermore, no such characteristic "hypochlorite" aroma is retained on the hands of the individual handling such laundry in both the wet and the dry states.

EXAMPLE XXII

AROMOX ® DMMC-W in various quantities is mixed with 0.1 grams of the compound having the structure:

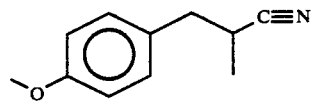

prepared according to Example II (bulked fractions 10–18). The resulting premix is then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Addition of Premix |
|---|---|
| 0.23% | Clear after three days. |
| 0.15% | Clear after three days. |
| 0.08% | Initially slightly turbid; two phases exist after three days. |

When the 5% aqueous sodium hypochlorite solutions are used as laundry bleaches, the resulting laundry batches on dry-out in an atmosphere of 65% relative humidity yields substantially no characteristic "hypochlorite" odor, but does have a sweet, anisic and animalic aroma. Furthermore, no such characteristic "hypochlorite" aroma is retained on the hands of the individual handling such laundry batches in both the wet and the dry states.

EXAMPLE XXIII

Two grams of AROMOX ® DMMC-W are admixed with eight drops of the compound having the structure:

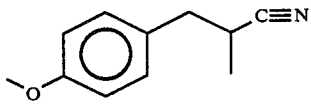

prepared according to Example II (bulked fractions 10–18). The premix is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain a sweet, anisic and animalic aroma profile whereas without the use of the the compound having the structure:

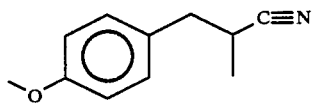

prepared according to Example II (bulked fractions 10–18), the bleached laundry batches have a faint characteristic disagreeable "hypochlorite" aroma.

EXAMPLE XXIV

Two grams of AROMOX ® DMMC-W are admixed with eight drops of the compound having the structure:

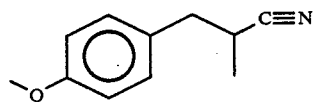

prepared according to Example II (bulked fractions 10–18). The premix is then added with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry batches on dry-out in an atmosphere of 50% relative humidity retain a sweet, anisic and animalic aroma profile whereas without the use of the compound having the structure:

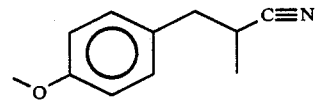

prepared according to Example II (bulked fractions 10–18), the bleached laundry batches have faint characteristic disagreeable "hypochlorite" aroma.

EXAMPLE XXV

Two grams of AROMOX ® DMMC-W are admixed with eight drops of either (a) the compound having the structure:

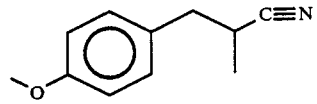

prepared according to Example II (bulked fractions 10–18); or (b) a 50–50 of the compound having the structure:

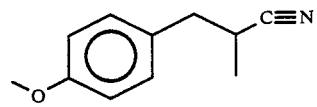

prepared according to Example II, bulked fractions 10–18 and diisoamylene epoxide produced according to Example II of application for U.S. Pat. No. 4,335,009 issued June 15, 1982 the disclosure of which is incorporated herein by reference. These premixes are then added with stirring to 200 grams of a mixture containing 4% aqueous sodium hypochlorite and 4% aqueous lithium hypochlorite. Sufficient 2M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atmosphere of 50% relative humidity have a sweet, anisic and animalic aroma (when using the compound having the structure:

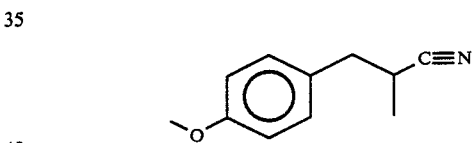

prepared according to Example II, bulked fractions 10–18 have a sweet, anisic and animalic aroma when using the mixture of the diisoamylene epoxide and the compound having the structure:

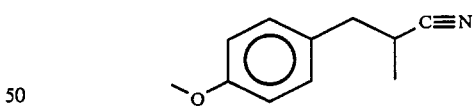

prepared according to Example II, bulked fractions 10–18; whereas without the use of the compound having the structure:

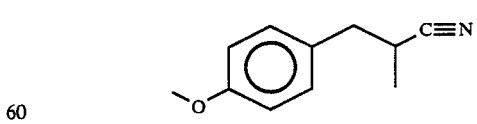

prepared according to Example II, bulked fractions 10–18 containing compositions of matter the bleached laundry batches have faint characteristic disagreeable "hypochlorite" aromas.

EXAMPLE XXVI

Four drops of the compound having the structure:

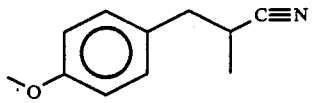

prepared according to Example II, bulked fractions 10–18 are added to 1.5 grams of AROMOX ® NCMD-W to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a sweet, anisic and animalic aroma. Furthermore, no such characteristic "hypochlorite" aroma is retained on the hands of the individual handling such laundry in both the wet and the dry states.

EXAMPLE XXVII

Four drops of the compound having the structure:

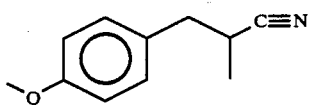

prepared according to Example II, bulked fractions 10–18 is added to 1 gram of n-undecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture to 12.8. The solution remains sustantially stable at 120° F. for a period of seven days. When the 5% aqueous sodium hypochlorite solution is used as a laundry bleach the resulting laundry on dry-out in an atmosphere of 65% relative humidity yields substantially no characteristic "hypochlorite" odor but does have a sweet, anisic and animalic aroma. Furthermore, no such characteristic "hypochlorite" aroma is retained on the hands of the individual handling such laundry in both the wet and the dry states.

EXAMPLE XXIII

One drop of n-tridecyl dimethyl amine oxide is admixed with eight drops of a 50:50 mixture of the diisoamylene epoxide prepared according to Example I(B) of application for U.S. Pat. No. 4,335,009 issued June 15, 1982 and the compound having the structure:

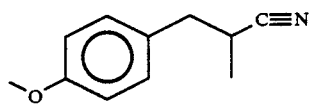

prepared according to Example II, bulked fractions 10–18, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity does have a sweet, anisic and animalic aroma; whereas without the use of the mixture of diisoamylene epoxide and the compound having the structure:

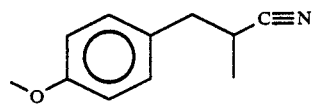

prepared according to Example II, bulked fractions 10–18, the bleached laundry has a faint characteristic disagreeable "hypochlorite" aroma.

EXAMPLE XXIX

AROMOX ® DMMC-W in various quantities is mixed with 0.1 gram of a 25:75 weight:weight mixture of diisoamylene epoxide:the compound having the structure:

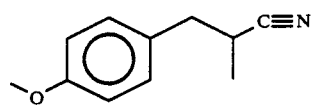

prepared according to Example II, bulked fractions 10–18. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Addition of Premix |
| --- | --- |
| 0.23% | Clear after three days. |
| 0.15% | Clear after three days. |
| 0.08% | Initially slightly turbid; two phases exist after three days. |

When used as laundry bleaches, the resulting bleached laundries on dry-out in an atmosphere of 50% relative humidity in each of the three cases above but does have a sweet, anisic and animalic "aroma" whereas without the use of the composition of matter set forth above containing diisoamylene epoxide and the compound having the structure:

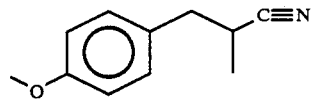

prepared according to Example II, bulked fractions 10–18, the bleached laundry has the same characteristic disagreeable "hypochlorite" aroma.

EXAMPLE XXX

DOWFAX ® 2A1 (see Note 1, infra) in various quantities, as set forth below, is mixed with 0.1 grams of a 50:50 mixture of (a) one of the diisoamylene epoxide compositions prepared according to Example II of application for U.S. Pat. No. 4,335,009 issued June 15, 1982 and (b) the compound having the structure:

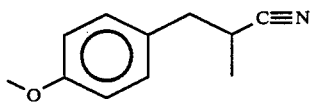

prepared according to Example II, bulked fractions 10–18. The resulting premixes are then added to 200 grams of an aqueous 7% sodium hypochlorite solution. Sufficient 12.5M aqueous sodium hydroxide is added to bring the pH of the mixture up to 13.5. The following results are obtained:

| Percentage of DOWFAX ® 2Al | Clarity of Hypochlorite Solution After Addition of Premix |
|---|---|
| 0.23% | Clear after seven days. |
| 0.15% | Clear after five days. |
| 0.08% | Clear after three days. |
| 0.01% | Initially slightly turbid; two phases exist after three days. |

Note 1: DOWFAX ® 2Al is a material consisting essentially of a compound defined according to the structure:

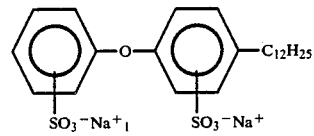

wherein the C$_{12}$H$_{25}$ moiety is branched chain and the SO$_3$⁻Na⁺ moieties are at various positions on each of the benzene rings.

EXAMPLE XXXI

DOWFAX ® 3B2 (see Note 2, infra) in various quantities as set forth below, is mixed with 0.1 gram of the compound having the structure:

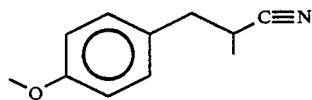

Note 2: DOWFAX ® 3B2 is a compound essentially defined according to the structure:

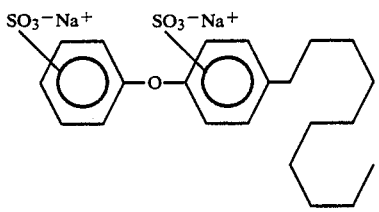

wherein the SO$_3$⁻Na$^{30}$ moieties are at various positions on the phenyl moieties. DOWFAX® 3B2 is a registered trademark of the Dow Chemical Company of Midland, Mich.

In the following examples, AROMOX ® DMC-W and AROMOX ® DMMC-W are 30% aqueous solutions of dimethyl cocoamine oxide; and AROMOX ® NCMDW is a 40% aqueous solution of N-cocomorpholine oxide produced by Armac Division of Akzo of Chicago, Ill. prepared according to Example I(B). The resulting premixes are then added to 200 grams of an aqueous 7% sodium hypochlorite solution. Sufficient 12.5M aqueous NaOH is added to bring the pH of the mixture up to 13.5. The following results are obtained:

| Percentage of DOWFAX ® 3B2 | Clarity of Hypochlorite Solution After Addition of Premix |
|---|---|
| 0.23% | Clear after seven days. |
| 0.15% | Clear after five days. |
| 0.08% | Clear after three days. |
| 0.01% | Clear after three days. Initially slightly turbid; two phases exist after three days. |

When the 7% aqueous sodium hypochlorite solutions are used as laundry bleaches, the resulting laundry batches on dry-out in an atmosphere of 65% relative humidity yield substantially no characteristic "hypochlorite" odors but does have a sweet, anisic and animalic aroma. Furthermore, no such characteristic "hypochlorite" aromas are retained on the hands of the individuals handling such laundry batches in both the wet and the dry states.

EXAMPLE XXXII

Four drops of a 25:75 weight/weight mixture of diisoamylene epoxide prepared according to Example II of application for U.S. Pat. No. 4,335,009 issued June 15, 1982 and the compound having the structure:

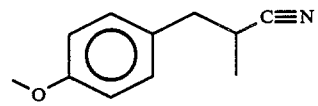

prepared according to Example II, bulked fractions 10–18, supra, is added to 2 grams of DOWFAX ® 3B2 and 0.5 grams of AROMOX ® DMC-W to produce a clear premix. The clear premix is added to 200 grams of CLOROX ® with stirring resulting in a clear stable single phase solution. Sufficient 1M aqueous NaOH is added to bring the pH of the mixture of 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a sweet, anisic and animalic aroma. Furthermore, no such characteristic "hypochlorite" aroma is retained on the hands of the individual handling such laundry in both the wet and the dry states.

EXAMPLE XXXIII

One gram of DOWFAX ® 3B2; one gram of DOWFAX ® 2A1 and 0.25 grams of AROMOX ® DMMC-W is admixed with eight drops of the compound having the structure:

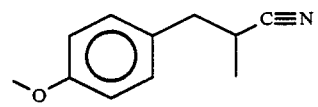

prepared according to Example II, bulked fractions 10-18. This premix is then added, with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity but does have a sweet, anisic and animalic aroma; whereas without the use of the compound having the structure:

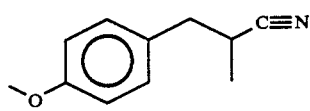

prepared according to Example II, bulked fractions 10-18, supra, the bleached laundry has a faint characteristic disagreeable "hypochlorite" aroma.

EXAMPLE XXXIV

One gram of DOWFAX® 2A1 and one gram of DOWFAX® 3B2 is admixed with eight drops of a 50:50 mixture of one of the diisoamylene epoxide compositions of Example II of application for U.S. Pat. No. 4,335,009 issued June 15, 1982 and the compound having the structure:

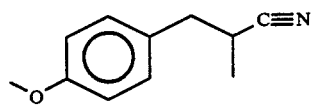

prepared according to Example II, bulked fractions 10-18. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity but does have a sweet, anisic and animalic aroma; whereas without the use of the perfume composition which is a mixture of diisoamylene epoxide and the compound having the structure:

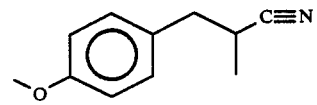

prepared according to Example II, bulked fractions 10-18, the bleached laundry has a faint characteristic disagreeable "hypochlorite" aroma.

EXAMPLE XXXV 1.5 Grams of DOWFAX® 2A1 is admixed with eight drops of the compound having the structure:

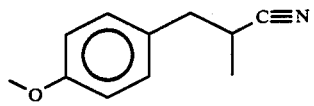

prepared according to Example II, bulked fractions 10-18, supra. This premix is then added with stirring to 200 grams of a mixture containing 4.5% aqueous sodiumn hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of two weeks. The resulting solution remains clear as a single phase when used as a laundry bleach. The resulting bleached laundry on dry-out in an atmosphere of 50% relative humidity does have a sweet, anisic and animalic aroma, whereas without the use of the compound having the structure:

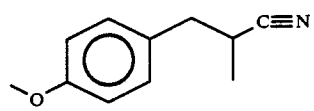

prepared according to Example II, bulked fractions 10-18, the bleached laundry has a faint characteristic disagreeable "hypochlorite" aroma.

EXAMPLE XXXVI

Four drops of a 50:50 mixture of one of the diisoamylene epoxide mixtures produced according to Example II of application for U.S. Pat. No. 4,335,009 issued June 15, 1982 and the compound having the structure:

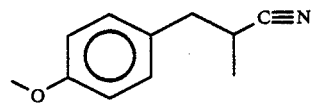

prepared according to Example II, bulked fractions 10-18, supra, is added to 1.0 grams of DOWFAX® 3B2 and 0.25 grams of AROMOX® NCMD-W to produce a clear premix. The clear premix is added to 200 grams of CLOROX® resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a sweet, anisic and animalic aroma. Furthermore, no such characteristic "hypochlorite" aroma is retained on the hands of the individual handling such laundry in both the wet and the dry states.

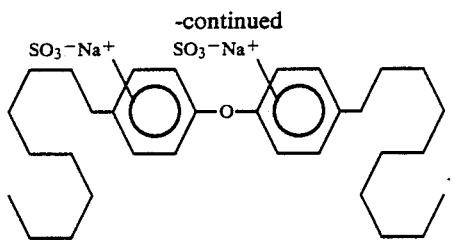

What is claimed is:

1. At least one 2-methyl-1-nitrilo- or 2-methyl-1-hydroxylamino-3-(methoxyphenyl) propane.

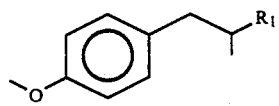

wherein $R_1$ is a nitrogen-containing moiety selected from the group consisting of:

(i) cyanide having the structure:

and (ii) hydroxylaminomethyl having the structure:

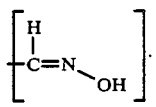

2. The 2-methyl-1-nitrilo or hydroxylamino-3-(methoxyphenyl)-substituted propane of claim 1 having the structure:

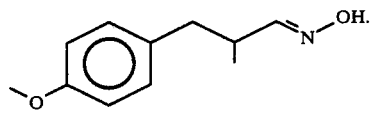

3. The 2-methyl-1-nitrilo or hydroxylamino-3-(methoxyphenyl)-substituted propane of claim 1 defined according to the structure:

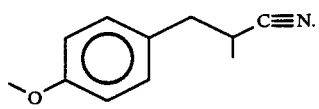

4. A process for augmenting or enhancing the aroma of a consumable material selected from the group consisting of perfume compositions, perfumed articles and perfumed polymers comprising the step of intimately admixing with said consumable material an aroma augmenting or enhancing quantity of at least one compound defined according to claim 1.

5. A process for augmenting or enhancing the aroma of a consumable material selected from the group consisting of perfume compositions, perfumed articles and perfumed polymers comprising the step of intimately admixing with said consumable material an aroma augmenting or enhancing quantity of at least one compound defined according to claim 2.

6. A process for augmenting or enhancing the aroma of a consumable material selected from the group consisting of perfume compositions, perfumed articles and perfumed polymers comprising the step of intimately admixing with said consumable material an aroma augmenting or enhancing quantity of at least one compound defined according to claim 3.

7. A chlorine-containing bleach composition comprising:
(a) a chlorine bleach base; and
(b) intimately admixed therewith at least one compound defined according to claim 1.

8. A perfumed aqueous alkali metal hypochlorite solution comprising as a sole detergent a composition of matter selected from the group consisting of (1) at least one substance defined according to the structure:

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl and the other of $R_1$ or $R_2$ is hydrogen; wherein $M_\alpha$ and $M_\beta$ are the same or different and each represents alkali metal selected from the group consisting of sodium, potassium and lithium and (2) a mixture comprising a material having the structure:

and intimately admixed therewith a substance having the structure:

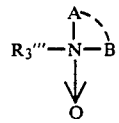

wherein $R_3'''$ is straight chain alkyl; wherein more than 55% of the $R_3'41$ moieties consist of straight chain alkyl having from 11 up to 13 carbon atoms and wherein "A" and "B" are each separately methyl up to 0.2% of one or more compatible perfume oils, said hypochlorite solution having a pH of 11 up to 14.0 and an aroma augmenting or enhancing quantity of at least one compound defined according to claim 1.

9. The composition of matter of claim 8 which is thickened using a thickening quantity of $C_{10}$–$C_{20}$ alkanoic acid salt thickener in a concentration such that the viscosity of the composition is 20–60 centipoises at a temperature of 20°–40° C.

10. The composition of claim 8 wherein the compound having the structure:

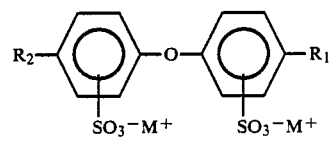

is selected from the group of materials having the structures;

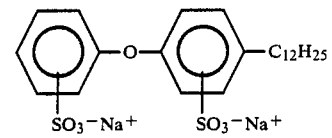

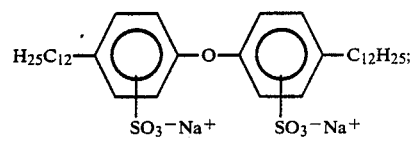

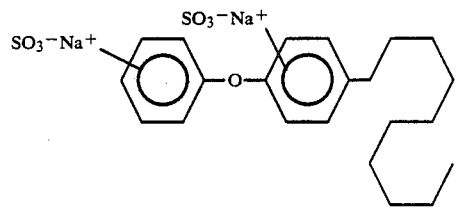

and